（12） United States Patent
Schaub et al.

(10) Patent No.: US 9,061,960 B2
(45) Date of Patent: Jun. 23, 2015

(54) METHOD FOR WORKING UP MIXTURES

(71) Applicant: BASF SE, Ludwigshafen (DE)

(72) Inventors: Thomas Schaub, Neustadt (DE); Pepa Dimitrova, Worms (DE); Rocco Paciello, Bad Duerkheim (DE); Frederic Bauer, Deidesheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/904,418

(22) Filed: May 29, 2013

(65) Prior Publication Data

US 2013/0324770 A1 Dec. 5, 2013

Related U.S. Application Data

(60) Provisional application No. 61/652,882, filed on May 30, 2012.

(51) Int. Cl.
*C07C 27/00* (2006.01)
*C07C 29/32* (2006.01)
*C07C 29/86* (2006.01)
*C07C 29/34* (2006.01)

(52) U.S. Cl.
CPC ............. *C07C 29/32* (2013.01); *C07C 29/86* (2013.01); *C07C 29/34* (2013.01)

(58) Field of Classification Search
CPC ...... C07C 31/125; C07C 29/32; C07C 29/34; C07C 29/86
USPC ........................................................ 568/902
See application file for complete search history.

(56) References Cited

U.S. PATENT DOCUMENTS

| 3,479,412 A | | 11/1969 | Pregaglia et al. | |
| 3,514,493 A | * | 5/1970 | Guglielmo et al. | 568/905 |
| 3,862,994 A | | 1/1975 | Yates | |
| 2010/0298613 A1 | * | 11/2010 | Tanaka et al. | 568/905 |

FOREIGN PATENT DOCUMENTS

EP  2 221 289 A1  8/2010

OTHER PUBLICATIONS

International Search Report issued Jul. 8, 2013, in PCT/EP2013/060651 (with English Translation of Category of Cited Documents).
U.S. Appl. No. 13/864,774, filed Apr. 17, 2013, Thomas Schaub, et al.
German Preliminary Search Report issued Oct. 22, 2012 in European Application 12 16 9997 ( with English translation of Cited Documents).

* cited by examiner

*Primary Examiner* — Yevegeny Valenrod
*Assistant Examiner* — Blaine G Doletski
(74) *Attorney, Agent, or Firm* — Oblon, McClelland, Maier & Neustadt, L.L.P.

(57) ABSTRACT

Method for working up a mixture comprising at least one alcohol of the general formula (I)

$$R^1-CH_2-CH_2-OH \quad (I)$$

or at least one branched alcohol of the general formula (II)

$$R^1-CH_2-CH_2-CHR^1-CH_2-OH \quad (II),$$

furthermore at least one oil-soluble complex compound of at least one metal of the 8th, 9th or 10th group of the Periodic Table of the Elements, which is selected from complex compounds which have at least one ligand $L^1$ which is at least bidentate, where at least one coordination site of $L^1$ is a nitrogen atom,
and at least one acid of the general formula (III)

$$R^1-CH_2-COOH \quad (III)$$

in the form of one of its salts,
where the groups $R^1$ are selected from $C_2$-$C_{10}$-alkyl, linear or branched,
wherein
  (a) the mixture is treated with water which can comprise an alkali metal hydroxide,
  (b) the salt or salts of acid of the general formula (III) are extracted.

20 Claims, No Drawings

METHOD FOR WORKING UP MIXTURES

The present invention relates to a method for working up a mixture comprising at least one alcohol of the general formula (I)

$$R^1-CH_2-CH_2-OH \qquad (I)$$

or at least one branched alcohol of the general formula (II)

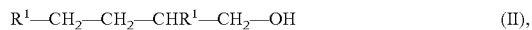

$$R^1-CH_2-CH_2-CHR^1-CH_2-OH \qquad (II),$$

1. furthermore at least one oil-soluble complex compound of at least one metal of the 8th, 9th or 10th group of the Periodic Table of the Elements, which is selected from complex compounds which have at least one ligand $L^1$ which is at least bidentate, where at least one coordination site of $L^1$ is a nitrogen atom, at least one acid of the general formula (III)

$$R^1-CH_2-COOH \qquad (III)$$

in the form of one of its salts,
where the groups $R^1$ are different or preferably identical and selected from $C_2$-$C_{10}$-alkyl, linear or branched,
wherein
 (a) the mixture is treated with water which can comprise an alkali metal hydroxide,
 (b) the salt or salts of acid of the general formula (III) are extracted.

Branched fatty alcohols find diverse uses as intermediates, for example for producing surfactants. It is therefore of interest to develop economical methods for producing branched fatty alcohols and in particular fatty alcohols branched in the 2 position. Of particular interest in this connection are methods for preparing Guerbet alcohols which have further branches besides the branching in position 2.

It is known from J. Org. Chem. 2006, 71, 8306 that Guerbet reactions can be catalyzed with the help of iridium complexes. Specifically, it is known from the cited passage that with the help of [Cp*IrCl$_2$]$_2$ and 1,7-octadiene and potassium tert-butanolate in p-xylene as solvent it is possible to dimerize the branched alcohol isoamyl alcohol to give the corresponding Guerbet alcohol (Cp*: pentamethylcyclopentadienyl). However, the yield is not optimal.

U.S. Pat. No. 3,514,493 discloses the preparation of 2-ethylhexanol and of 2-butyloctanol with the help of supported metals, for example with the help of palladium or ruthenium supported on activated carbon. J. Organomet. Chem. 1972, 37, 385 proposes that Guerbet alcohols can be made with the help of RuCl$_3$ with certain phosphane ligands in homogeneous phase.

Work-up of the reaction mixture takes place in many cases by distillation. Firstly, unconsumed starting material is distilled off, then the desired Guerbet alcohol. In most cases, the catalyst remains undamaged, meaning that it is possible to add alcohol and fresh base and to leave the Guerbet reaction to run again. If the Guerbet reaction is carried out in several cycles—thus for example implementation of the actual reaction, distillative work-up, addition of alcohol as starting material, implementation of the actual reaction, distillative work-up etc.—it is often observed that conversion and yield per cycle are reduced. As a result, the efficiency of the catalyst diminishes which, in view of the high cost of many catalysts (central metal, ligand), is disadvantageous. It can also be observed that after several cycles, an ever further increasing fraction of solids remains in the reaction vessel; this hinders the thorough mixing of the reaction mixture.

It was therefore the object to provide a method by means of which the disadvantages discussed above can be avoided. Such a method should be simple to carry out and produce a catalyst-containing mixture which can be used rapidly again for the synthesis of Guerbet alcohols.

Accordingly, the method defined at the start for working up mixtures has been found, also called method according to the invention for short.

The method according to the invention starts from at least one mixture which comprises a plurality of constituents. One constituent is at least one alcohol of the general formula (I)

$$R^1-CH_2-CH_2-OH \qquad (I)$$

in which $R^1$ is selected from $C_2$-$C_{10}$-alkyl, linear or—if possible—branched, i.e. ethyl, n-propyl, isopropyl, n-butyl, isobutyl, sec-butyl, n-pentyl, n-hexyl, n-heptyl, n-octyl, n-decyl, preferably ethyl and isopropyl, very particularly preferably isopropyl.

In one preferred embodiment of the present invention, $R^1$ is selected from ethyl, n-propyl, n-butyl and isopropyl.

Alcohol of the general formula (I) can be present in pure form or in the form of mixtures, in particular in the form of isomer mixtures, in particular in the form of mixtures with at least one isomeric alcohol. In this connection, in the case of $R^1$=propyl, the isomeric alcohol(s) can correspond to the formula (I). In a particular variant of the present invention, alcohol of the general formula (I) is present in the mixture with at least one such isomeric alcohol which does not correspond to the formula (I).

An example of a suitable isomeric alcohol of isoamyl alcohol ($R^1$=isopropyl) is 2-methylbutanol. This reacts with isoamyl alcohol preferably to give an alcohol of the formula (IV.1a)

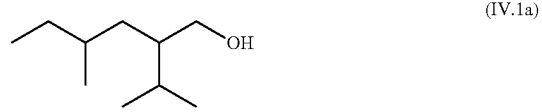

(IV.1a)

In one embodiment of the present invention, alcohol of the formula (I) is present in a mixture with 0.1 to 25 mol % of at least one isomeric alcohol which can, but preferably does not, correspond to the formula (I).

Alcohol of the general formula (I) and in particular mixtures of alcohol of the general formula (I) with one or more of its isomers can be prepared by synthesis or on the basis of biological raw materials, for example by fermentation or other biological degradation of saccharides.

Mixture used according to the invention furthermore comprises at least one oil-soluble complex compound of at least one metal of the 8th, 9th or 10th group of the Periodic Table of the Elements, also called "complex" for short, which is selected from complex compounds which have at least one ligand $L^1$ which is at least bidentate, where at least one coordination site of $L^1$ is a nitrogen atom.

In one embodiment of the present invention, "oil-soluble" is understood as meaning that the solubility of the complex in at least one of the solvents toluene, m-xylene, n-hexane or alcohol of the general formula (I) or branched alcohol of the general formula (II) is at least 0.5 g/l, measured at room temperature. At least one of the complexes serves as catalyst. In this connection, it is possible for two or more oil-soluble complex compounds of metal of the 8th, 9th or 10th group of the Periodic Table of the Elements to be present in the reaction mixture but for only one of them to be catalytically active.

In one embodiment of the present invention, "oil-soluble" is understood as meaning that complex at 25° C. has a Nernst distribution coefficient of at least 3, preferably at least 5, particularly preferably at least 10, very particularly preferably at least 20, very particularly preferably up to 1 000 000, based on at least one of the solvents toluene, m-xylene, n-hexane or alcohol of the general formula (I) or branched alcohol of the general formula (II) on the one hand and water on the other hand.

Complex has at least one metal of the 8th, 9th or 10th group of the Periodic Table of the Elements and at least one ligand $L^1$. Metals of the 8th, 9th or 10th group are selected from iron, cobalt, nickel, ruthenium, rhodium, iridium, osmium, palladium and platinum, preferably iridium and particularly preferably ruthenium. Iridium is preferably present as iridium(I) or iridium(III), ruthenium preferably as Ru(0), Ru(III) and particularly preferably as Ru(II).

In one embodiment of the present invention, complex has at least one ligand $L^1$. Here, ligand $L^1$ is coordinated via two, three or four nitrogen atoms with the central metal, i.e. with metal of the 8th, 9th or 10th group of the Periodic Table of the Elements, preferably with iridium or ruthenium and in particular with Ru(II), preferably via two or three, and $L^1$ has no coordination sites different from nitrogen. An example of a bidentate ligand $L^1$ which coordinates with Ru(II) via two nitrogen atoms and has no coordination sites different from nitrogen is 2,2'-bipyridyl.

In another embodiment of the present invention, ligand $L^1$ is coordinated via two or three coordination sites with the central metal, i.e. with metal of the 8th, 9th or 10th group of the Periodic Table of the Elements, preferably with iridium or ruthenium and in particular with Ru(II), of which one or two coordination site(s) is/are different from nitrogen and the other(s) is/are nitrogen atom(s). Coordination sites of ligand $L^1$ different from nitrogen are selected from phosphorus atoms, oxygen atoms, sulfur atoms and in particular carbene carbon atoms.

Nitrogen atoms which coordinate to central metal are preferably selected here from tertiary amine nitrogen atoms which are part of a heterocycle', and nitrogen atoms which are part of a tertiary amino group which is not part of a heterocycle'.

In one embodiment of the present invention, L' is selected from compounds of the general formula (V)

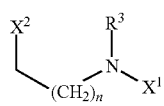

(V)

where the variables are selected as follows:
$R^3$ is selected from
  hydrogen,
  $C_1$-$C_{10}$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl; preferably n-$C_1$-$C_4$-alkyl such as methyl, ethyl, n-propyl, n-butyl, in particular methyl;
  $C_3$-$C_{10}$-cycloalkyl, for example cyclopropyl, cyclobutyl, cyclopentyl, cyclohexyl, cycloheptyl, cyclooctyl, cyclononyl and cyclodecyl, preferably $C_5$-$C_7$-cycloalkyl, in each case unsubstituted or mono- or polysubstituted, for example with methyl, methoxy or ethyl, n is selected from zero and one,
$X^1$ is selected from
  hydrogen,
  $C_1$-$C_5$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, in particular methyl or isopropyl, and
  $(CH_2)_{n+1}$—$X^2$,
$X^2$ is selected from $NR^4R^5$, 2-pyridyl and imidazol-2-ylidenyl of the formula

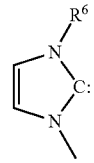

$R^4$, $R^5$ are different or preferably identical and selected from $C_1$-$C_{10}$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl; preferably tert-butyl or n-$C_1$-$C_4$-alkyl such as methyl, ethyl, n-propyl, n-butyl, in particular tert-butyl or methyl;
  $C_3$-$C_{10}$-cycloalkyl, for example cyclopropyl, cyclobutyl, cyclopentyl, cyclohexyl, cycloheptyl, cyclooctyl, cyclononyl and cyclodecyl, preferably $C_5$-$C_7$-cycloalkyl, in each case unsubstituted or mono- or polysubstituted, for example with methyl, methoxy or ethyl,
  benzyl and
  phenyl, unsubstituted or mono- or polysubstituted with $C_1$-$C_3$-alkyl, for example para-methylphenyl, para-ethylphenyl, 2,6-dimethylphenyl, 2,4,6-trimethylphenyl, 2,6-diethylphenyl, 2,6-diisopropylphenyl and 2-methyl-4-isopropylphenyl,
$R^6$ is selected from $C_1$-$C_{10}$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl; preferably n-$C_1$-$C_4$-alkyl such as methyl, ethyl, n-propyl, n-butyl, in particular methyl;
  $C_3$-$C_{10}$-cycloalkyl, for example cyclopropyl, cyclobutyl, cyclopentyl, cyclohexyl, cycloheptyl, cyclooctyl, cyclononyl and cyclodecyl, preferably $C_5$-$C_7$-cycloalkyl, in each case unsubstituted or mono- or polysubstituted, for example with methyl, methoxy or ethyl,
  benzyl and
  phenyl, unsubstituted or mono- or polysubstituted with $C_1$-$C_3$-alkyl, for example para-methylphenyl, para-ethylphenyl, 2,6-dimethylphenyl, 2,4,6-trimethylphenyl, 2,6-diethylphenyl, 2,6-diisopropylphenyl and 2-methyl-4-isopropylphenyl.

In one embodiment of the present invention, $L^1$ is selected from compounds of the general formula (VI)

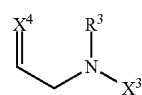

(VI)

where the variables are selected as follows:
R³ is selected from
  hydrogen,
  $C_1$-$C_{10}$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl; preferably n-$C_1$-$C_4$-alkyl such as methyl, ethyl, n-propyl, n-butyl, in particular methyl;
  $C_3$-$C_{10}$-cycloalkyl, for example cyclopropyl, cyclobutyl, cyclopentyl, cyclohexyl, cycloheptyl, cyclooctyl, cyclononyl and cyclodecyl, preferably $C_5$-$C_7$-cycloalkyl, in each case unsubstituted or mono- or polysubstituted, for example with methyl, methoxy or ethyl,
  benzyl and
  phenyl, unsubstituted or mono- or polysubstituted with $C_1$-$C_3$-alkyl, for example para-methylphenyl, para-ethylphenyl, 2,6-dimethylphenyl, 2,4,6-trimethylphenyl, 2,6-diethylphenyl, 2,6-diisopropylphenyl and 2-methyl-4-isopropylphenyl,
X³ is selected from
  hydrogen,
  $C_1$-$C_5$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl; preferably n-$C_1$-$C_4$-alkyl such as methyl, ethyl, n-propyl, n-butyl, in particular methyl, and
  $CH_2$=$X^4$,
X⁴ is selected from NR⁴, and
R⁴ is selected from
  $C_1$-$C_{10}$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl; preferably tert-butyl or n-$C_1$-$C_4$-alkyl such as methyl, ethyl, n-propyl, n-butyl, in particular methyl or tert-butyl,
  $C_3$-$C_{10}$-cycloalkyl, for example cyclopropyl, cyclobutyl, cyclopentyl, cyclohexyl, cycloheptyl, cyclooctyl, cyclononyl and cyclodecyl, preferably $C_5$-$C_7$-cycloalkyl, in each case unsubstituted or mono- or polysubstituted, for example with methyl, methoxy or ethyl,
  benzyl and
  phenyl, unsubstituted or mono- or polysubstituted with $C_1$-$C_3$-alkyl, for example para-methylphenyl, para-ethylphenyl, 2,6-dimethylphenyl, 2,4,6-trimethylphenyl, 2,6-diethylphenyl, 2,6-diisopropylphenyl and 2-methyl-4-isopropylphenyl.

In one embodiment of the present invention, L¹ is selected from compounds of the general formula (VII)

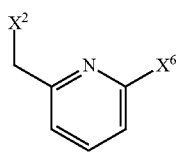

(VII)

where the variables are selected as follows:
X⁶ is selected from hydrogen,
  $C_1$-$C_5$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl; preferably n-$C_1$-$C_4$-alkyl such as methyl, ethyl, n-propyl, n-butyl, in particular methyl, and
  $CH_2$—$X^2$,
X² is selected from NR⁴R⁵, 2-pyridyl and imidazol-2-ylidenyl of the formula

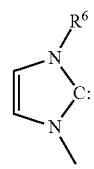

R⁴, R⁵ are different or preferably identical and selected from $C_1$-$C_{10}$-alkyl, $C_3$-$C_{10}$-cycloalkyl, benzyl and phenyl, unsubstituted or mono- or polysubstituted with $C_1$-$C_3$-alkyl,
R⁶ is selected from $C_1$-$C_{10}$-alkyl, $C_3$-$C_{10}$-cycloalkyl, benzyl and phenyl, unsubstituted or mono- or polysubstituted with $C_1$-$C_3$-alkyl.
R³, R⁴, R⁵ and R⁶ are as defined in more detail above.

In one embodiment of the present invention, L¹ is selected from compounds of the general formula (VIII)

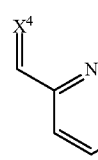

(VIII)

where the variables are selected as follows:
X³ is selected from hydrogen, $C_1$-$C_5$-alkyl and $CH_2$=$X^4$,
X⁴ is identical or optionally different, preferably identical, and selected from N—R⁴,
R⁴ is $C_1$-$C_{10}$-alkyl, $C_3$-$C_8$-cycloalkyl, benzyl or phenyl, unsubstituted or mono- or polysubstituted with $C_1$-$C_3$-alkyl.

In one embodiment of the present invention, L¹ is selected from compounds of the general formula (IX)

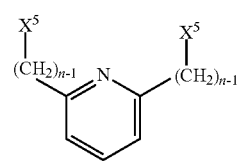

(IX)

where the variables are selected as follows:
n is different or preferably identical and in each case zero or one
X⁵ is in each case identical and selected from NR⁴R⁵, 2-pyridyl and imidazol-2-ylidenyl of the formula

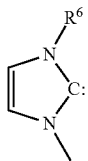

$R^4$, $R^5$ are different or identical and selected from hydrogen, $C_1$-$C_{10}$-alkyl, $C_3$-$C_{10}$-cycloalkyl, benzyl and phenyl, unsubstituted or mono- or polysubstituted with $C_1$-$C_3$-alkyl, $R^6$ is selected from $C_1$-$C_{10}$-alkyl, $C_3$-$C_{10}$-cycloalkyl, benzyl and phenyl, unsubstituted or mono- or polysubstituted with $C_1$-$C_3$-alkyl.

$R^3$, $R^4$, $R^5$ and $R^6$ are as defined in more detail above.

Particularly preferred examples of ligands $L^1$ are those of the formula (IX.1)

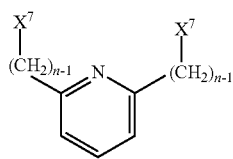

(IX.1)

in which the groups $(CH_2)_{n-1}$—$X^7$ are in each case identical and selected from 2-pyridyl (i.e. in each case n=zero), $CH_2$—$N(CH_3)_2$, $CH_2$—$N(C_2H_5)_2$, $CH_2$—$N(n-C_3H_7)_2$, $CH_2$—$N(n-C_4H_9)_2$, $CH_2$—$N(iso-C_3H_7)_2$, $CH_2$—$N(tert-C_4H_9)_2$, $CH_2$—$N(n-C_5H_{11})_2$, $CH_2$—$N(n-C_6H_{13})_2$, $CH_2$—$N(n-C_8H_{17})_2$, $CH_2$—$N(C_6H_5)_2$, $CH_2$—$N(CH_2$—$C_6H_5)_2$, and $CH_2$—$N(cyclo-C_6H_{11})_2$, (i.e. in each case n=1), and

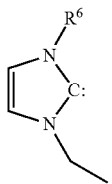

(i.e. in each case n=1), where $R^7$ is selected from methyl, ethyl, n-propyl, isopropyl, n-butyl, n-pentyl, n-hexyl, n-heptyl, n-octyl, preferably isopropyl or n-$C_1$-$C_4$-alkyl such as methyl, ethyl, n-propyl, n-butyl, in particular methyl, cyclohexyl and phenyl, unsubstituted or mono- or up to trisubstituted with identical or different $C_1$-$C_3$-alkyl, for example para-methylphenyl, 2,6-dimethylphenyl, 2,4,6-trimethylphenyl, 2,6-diethylphenyl, 2,6-diisopropylphenyl and 2-methyl-4-isopropylphenyl.

Other particularly preferred examples of ligands $L^1$ are those of the formula (VIII.1)

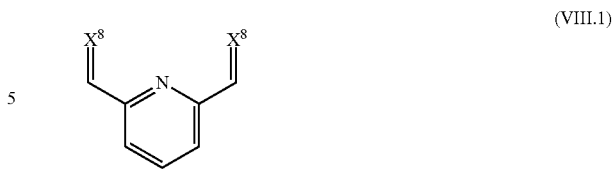

(VIII.1)

in which $X^8$ are in each case identical and selected from N—$CH_3$, N—$C_2H_5$, N-n-$C_3H_7$, N-n-$C_4H_9$, N-iso-$C_3H_7$, N-n-$C_5H_{11}$, N-n-$C_6H_{13}$, N-n-$C_8H_{17}$, N—$CH_2$—$C_6H_5$ and N-cyclo-$C_6H_{11}$, and N-phenyl, unsubstituted or mono- or up to trisubstituted with identical or different $C_1$-$C_3$-alkyl, for example N-para-methylphenyl, N-2,6-dimethylphenyl, N-2,4,6-trimethylphenyl, N-2,6-diethylphenyl, N-2,6-diisopropylphenyl and N-(2-methyl-4-isopropylphenyl).

A very particularly preferred ligand $L^1$ is 2,6-bis-2-pyridylpyridine, within the context of the present invention also called "terpyridyl" for short.

In one embodiment of the present invention, complex can have at least one further ligand selected from CO, pseudohalides, organic carbonyl compounds, aromatics, olefins, phosphanes, hydride and halides.

Here, "at least one further ligand" is to be understood as meaning a ligand which is different from ligand $L^1$. Examples of further ligands are CO (carbon monoxide), pseudohalide, in particular cyanide, isocyanate and rhodanide, organic carbonyl compounds, for example ketones, preferably organic dicarbonyl compounds such as acetyl acetonate, 1-phenylbutane-1,3-dione, acetic ester, aromatics which may be electrically charged or uncharged. Preferred examples of uncharged aromatics are benzene, toluene, para-xylene, hexamethylbenzene and para-cymene. Preferred examples of electrically charged aromatics are negatively charged aromatics, in particular cyclopentadienyl, indenyl, 4,5-benzindenyl and Cp* (pentamethylcyclopentadienyl), olefins, electrically neutral or as anion, for example COD (1,5-cyclooctadienyl), COE (cyclooctenyl), allyl or methallyl (2-methylallyl), phosphanes, for example mono-, di- or triphosphanes, preferably monophosphanes, in particular tertiary aromatic phosphanes, for example triphenylphosphane, hydride and halides, for example bromide and in particular chloride.

Examples of phosphanes suitable as further ligand are those which have at least one unbranched or branched $C_1$-$C_{12}$-alkyl radical, at least one $C_3$-$C_{12}$-cycloalkyl radical or at least one aromatic radical having up to 24 carbon atoms. Examples of $C_1$-$C_{12}$-alkyl radicals are methyl, ethyl, 1-propyl, 2-propyl, 1-butyl, 2-butyl, 1-(2-methyl)propyl, 2-(2-methyl)propyl, 1-pentyl, 1-hexyl, 1-heptyl, 1-octyl, 1-nonyl, 1-decyl, 1-undecyl, 1-dodecyl, 1-(2-methyl)pentyl, 1-(2-ethyl)hexyl, 1-(2-n-propyl)heptyl. Preferred $C_1$-$C_{12}$-alkyl radicals are selected from ethyl, 1-butyl, sec-butyl and 1-octyl.

Examples of $C_3$-$C_{12}$-cycloalkyl radicals are in particular selected from $C_4$-$C_8$-cycloalkyl radicals, branched or unbranched, such as cyclopentyl, cyclohexyl, cycloheptyl, cyclooctyl, methylcyclopentyl, for example 2-methylcyclopentyl, 3-methylcyclopentyl, also 2,5-dimethylcyclopentyl (syn, anti or as isomer mixture), 2-methylcyclohexyl, 3-methylcyclohexyl, 4-methylcyclohexyl, 2,6-dimethylcyclohexyl (syn, anti or as isomer mixture), norbonyl and —CH$_2$—C$_6$H$_{11}$. A preferred C$_3$-C$_{12}$-cycloalkyl radical is cyclohexyl.

In a preferred variant, the further ligand selected is a phosphane which carries two, particularly preferably three identical radicals, for example tri-n-butylphosphane, tri-sec-butylphosphane, tricyclohexylphosphane or tri-n-octylphosphane.

In one embodiment, the substituents of phosphane suitable as a further ligand that are selected are at least one aromatic radical, for example 9-anthracenyl, preferably three identical aromatic radicals, for example phenyl, 2-tolyl, 3-tolyl, para-tolyl, xylyl, 1-naphthyl, 2-naphthyl, 1-binaphthyl, para-anisyl, 2-ethylphenyl, 3-ethylphenyl, para-ethylphenyl, 2-chlorophenyl, para-chlorophenyl, 2,6-dichlorophenyl, or at least one heteroaromatic radical. Examples of heteroaromatic radicals are thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolinyl, quinolinyl, acridinyl, naphthyridinyl, quinoxalinyl, quinazolinyl, cinnolinyl, piperidinyl, carbolinyl, thiazolyl, oxazolyl, isothiazolyl, isoxazolyl. The heteroaryl groups can be unsubstituted or substituted with one or more substituents which are defined above under C$_1$-C$_{12}$-alkyl.

In another preferred variant, the further ligand selected is a polydentate phosphane, for example with the grouping >P—CH$_2$—CH$_2$—P(C$_1$-C$_{10}$-alkyl)-CH$_2$CH$_2$—P<, particularly preferably with the grouping >P—CH$_2$—CH$_2$—P<. An example is 1,2-bis(dicyclohexylphosphino)ethane.

It has now been observed that the by-products which are formed during the Guerbet reaction, for example at least one acid of the general formula (III)

R$^1$—CH$_2$—COOH  (III)

in the form of one of its salts, for example in the form of its ammonium salts or preferably alkali metal salts, particularly preferably in the form of its sodium or potassium salts, remain in the reaction vessel on account of their high boiling point. The mixture which is worked up according to the invention thus comprises at least one acid of the general formula (III) in the form of one or more of its salts.

Here, R$^1$ is as defined above, and R$^1$ in acid of the general formula (III) corresponds to R$^1$ in alcohol of the formula (I).

In one embodiment of the present invention, the mixture which is worked up according to the invention can comprise at least one branched alcohol of the general formula (II).

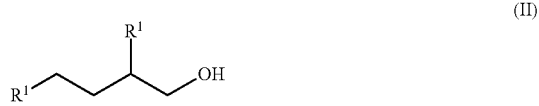

(II)

Here, R$^1$ is as defined above and corresponds in each case to R$^1$ in alcohol(s) of the formula (I).

In one embodiment of the present invention, the mixture which is worked up according to the invention can comprise at least one ester of the general formula (IV)

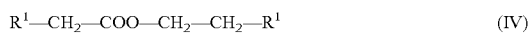

R$^1$—CH$_2$—COO—CH$_2$—CH$_2$—R$^1$  (IV)

Mixture to be worked up according to the invention can comprise at least one solvent which is different from alcohol of the general formula (I), for example an aromatic solvent such as, for example, para-xylene, ortho-xylene, meta-xylene, isomer mixtures of xylene, mesitylene, or toluene, ethylbenzene or aliphatic or cycloaliphatic solvents such as, for example, n-hexane, n-heptane, n-octane, n-nonane, n-dodecane or decalin. In one preferred embodiment of the present invention, the mixture comprises no solvent which is different from alcohol of the general formula (I) and branched alcohol of the general formula (II).

In one embodiment of the present invention, the starting mixture used has acid of the general formula (III) on the one hand and alcohol of the general formula (I) and/or branched alcohol of the general formula (II) on the other hand in a weight ratio in the range from 1:100 to 1:1, preferably 1:5 to 1:1.05, i.e. acid (III) to total (weight) of alcohol (I) and/or branched alcohol (II) is in the range from 1:100 to 1:1, preferably 1:5 to 1:1.05.

In one embodiment of the present invention, the starting mixture is a suspension. Thus, it is for example possible for salt of acid of the general formula (III) to be present as solid precipitate. In another embodiment, the starting mixture is one which is a solution that appears to be homogeneous to the naked eye.

According to the invention, mixture described above is treated in a step (a) firstly with water which can comprise one or more alkali metal hydroxides, for example sodium hydroxide or potassium hydroxide. In another variant, treatment is with water which is free from salt, or—in a further variant—with water with a neutral pH but which can comprise salts such as, for example, sodium chloride.

For the treatment according to step (a), mixture to be treated is admixed with water and mixed, for example over a period from 5 seconds up to half an hour. Mixing can be for example by means of shaking or preferably by means of stirring.

In one embodiment of the present invention in step (a), admixing is with water and with alcohol of the general formula (I), for example in a volume ratio in the range from 5:1 to 1:5.

In one embodiment of the present invention, in step (a), water on the one hand and mixture comprising alcohol of the general formula (I) or branched alcohol of the general formula (II), furthermore oil-soluble complex compound and acid of the formula (III) on the other hand are used in a volume ratio in the range from 10:1 to 1:10, preferably in a volume ratio in the range from 5:1 to 1:5.

In a preferred embodiment of the present invention, in step (a), water and mixture comprising alcohol of the general formula (I) or branched alcohol of the general formula (II), furthermore oil-soluble complex compound, and acid of the formula (III) are used in a volume ratio in the range from 0.5:1 to 2:1.

In step (a), in many cases no homogeneous mixture is formed, but instead it is observed that two different liquid phases separate. Here, the organic phase is in many cases colored.

In other cases, in step (a), a homogeneous phase is formed which can be converted to a two-phase mixture by adding water or further alcohol of the general formula (I).

In step (b), the salt or salts of acid of the general formula (III) are extracted. This is to be understood as meaning that the phase separation of aqueous phase in which the salt or salts of acid of the general formula (III) have become enriched is awaited and then the aqueous phase is separated off, for example by means of a separating funnel (laboratory) or by means of the bottom discharge valve, into a larger vessel, for example a stirred-tank reactor or autoclave.

In one embodiment of the present invention, salt of acid of the general formula (III) in mixtures of water and alcohol of the general formula (I) or water and branched alcohol of the general formula (II) has a Nernst distribution coefficient in the range from 100 to 3, determined at room temperature.

In one embodiment of the present invention, steps (a) and (b) are repeated one or more times, for example three times. In another embodiment of the present invention, steps (a) and (b) are applied only once in each case before the actual Guerbet reaction is started again.

In one embodiment of the present invention, the method according to the invention is carried out at a temperature in the range from 5 to 60° C., preferably up to 40° C. This refers to the temperature after step (a).

In one embodiment of the present invention, in step (a), it is possible to start from a mixture which has a temperature above 60° C., for example up to 85° C. or up to 70° C., and cools this mixture by adding water which has a temperature in the range from 10 to 20° C. to a temperature of 60° C. or less.

In one embodiment of the present invention, alcohol of the general formula (I) is also added before or after or together with the addition of water in step (a). The procedure is preferably such that the volume ratio of organic phase to aqueous phase, i.e. of mixture comprising alcohol of the general formula (I) and/or branched alcohol of the general formula (II), oil-soluble complex compound, establishes in a volume ratio in the range from 5:1 to 1:5.

In one embodiment of the present invention, steps (a) and (b) of the method according to the invention are carried out at atmospheric pressure. In another embodiment of the present invention, at least one of steps (a) and (b) is carried out at increased pressure, for example step (b) can be carried out at a pressure in the range from 1.1 to 5 bar.

As a result of implementing the method according to the invention it is possible to readily and rapidly remove by-products of the Guerbet reaction and in particular acid of the general formula (III) in the form of its salts from the mixture to be worked-up. It gives a mixture which comprises complex virtually quantitatively and in active form and which can be readily mixed again. By adding alcohol of the general formula (I) and optionally base, it is possible to start the Guerbet reaction again.

In one embodiment of the present invention, distillation is carried out before the mixture worked-up by the method according to the invention is used again for a Guerbet reaction to initially at least partially remove the water remaining as a result of steps (a) and (b) and in the organic phase, for example by azeotropic distillation with alcohol of the general formula (I), and only then is alcohol of the general formula (I) and optionally base added in order to start the Guerbet reaction again.

The present invention further provides a method for preparing branched alcohols of the general formula (II)

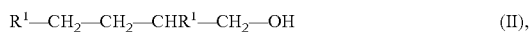

also called synthesis method according to the invention for short, by reacting at least one alcohol of the general formula (I)

where the groups $R^1$ can be different or preferably identical and are selected from $C_2$-$C_{10}$-alkyl, linear or branched, in the presence of at least one oil-soluble complex compound of at least one metal of the 8th, 9th or 10th group of the Periodic Table of the Elements, wherein by-products selected from acid of the general formula (III)

are separated off in the form of one of its salts by the method according to the invention described above.

The synthesis method according to the invention starts from at least one alcohol of the general formula (I) which is described above. According to the invention, said alcohol is reacted with catalysis by at least one oil-soluble complex compound of at least one metal of the 8th, 9th or 10th group of the Periodic Table of the Elements. Oil-soluble complex compound of at least one metal of the 8th, 9th or 10th group of the Periodic Table of the Elements is as defined above.

The reaction in accordance with the synthesis method according to the invention takes place in the presence of at least one base. Preferred bases are Brönsted bases. Examples of suitable bases which may be mentioned are: LiOH, NaOH, KOH, LiH, NaH, KH, Ca(OH)$_2$, CaH$_2$, LiAlH$_4$, NaBH$_4$, LiBH$_4$, Na$_2$CO$_3$, NaHCO$_3$, Li$_2$CO$_3$, LiHCO$_3$, K$_2$CO$_3$, KHCO$_3$, K$_3$PO$_4$, Na$_3$PO$_4$, n-butyllithium, tert-BuLi, methyllithium, phenyllithium, lithium methanolate, lithium ethanolate, LiO-n-C$_3$H$_7$, LiO-iso-C$_3$H$_7$, LiO-n-C$_4$H$_9$, LiO-iso-C$_4$H$_9$, LiO-n-C$_5$H$_{11}$, LiO-iso-C$_5$H$_{11}$, LiO-n-C$_6$H$_{13}$, LiO-iso-C$_6$H$_{13}$, lithium n-heptanolate, lithium n-octanolate, lithium benzylate, lithium phenolate, potassium methanolate, potassium ethanolate, KO-n-C$_3$H$_7$, KO-iso-C$_3$H$_7$, KO-n-C$_4$H$_9$, KO-iso-C$_4$H$_9$, KO-tert-C$_4$H$_9$, KO-n-C$_5$H$_{11}$, KO-iso-C$_5$H$_{11}$, KO-n-C$_6$H$_{13}$, KO-iso-C$_6$H$_{13}$, potassium n-heptanolate, potassium n-octanolate, potassium benzylate, potassium phenolate, sodium methanolate, sodium ethanolate, NaO-n-C$_3$H$_7$, NaO-iso-C$_3$H$_7$, NaO-n-C$_4$H$_9$, NaO-iso-C$_4$H$_9$, NaO-tert-C$_4$H$_9$, NaO-n-C$_5$H$_{11}$, NaO-iso-C$_5$H$_{11}$, NaO-n-C$_6$H$_{13}$, NaO-iso-C$_6$H$_{13}$, sodium n-heptanolate, sodium n-octanolate, sodium benzylate, sodium phenolate, KN(SiMe$_3$)$_2$, LiN(SiMe$_3$)$_2$, NaN(SiMe$_3$)$_2$, NH$_3$ and amines of the formula $(R^8)_a NH_{3-a}$, where a is selected from 1, 2 and 3, and $R^8$=identical or different and independently of one another unsubstituted or at least monosubstituted $C_1$-$C_{10}$-alkyl, (—C$_1$-C$_4$-alkyl-P(phenyl)$_2$), $C_3$-$C_{10}$-cycloalkyl, $C_3$-$C_{10}$-heterocyclyl, where $C_3$-$C_{10}$-heterocyclyl is to be understood as meaning those cyclic groups which have 3 to 10 carbon atoms and at least one heteroatom selected from N, O and S, also $C_5$-$C_{14}$-aryl or $C_5$-$C_{10}$-heteroaryl, where $C_5$-$C_{10}$-heteroaryl has at least one heteroatom selected from N, O and S.

In one embodiment of the present invention, in total 0.01 to 50% by weight of base is used, preferably 0.5 to 15% by weight, based on the total alcohol of the formula (I) used.

In one embodiment of the present invention, the reaction mixture is liquid at reaction temperature. In this connection, within the context of the present invention, it is possible for alcohol of the general formula (I) or at least one of its isomers to be present at least partially in the gas phase.

In one embodiment of the present invention, the reaction in accordance with the synthesis method according to the invention is carried out at a temperature in the range from 80 to 200° C., preferably 100 to 200° C., particularly preferably in the range from 110 to 170° C.

In one embodiment of the present invention, the catalysis is homogeneous catalysis. Homogeneous catalysis is understood as meaning that the catalyst is not used in a form deposited on a solid support and that no emulsion is produced in which the reactants react with one another. Here, the catalyst or catalysts are dissolved completely or at least predominantly in the reaction mixture, for example to at least 90 mol %, preferably to at least 95 mol %, based on the respective metal of the 8th, 9th or 10th group of the Periodic Table of the Elements.

In one embodiment of the present invention, the reaction in accordance with the synthesis method according to the invention is carried out in the presence of at least one inert gas. Suitable inert gases are selected from nitrogen and noble gases, in particular argon. In another embodiment of the present invention, the process according to the invention is carried out in the presence of hydrogen. In a further embodiment, the method according to the invention is carried out in the presence of a mixture of hydrogen and at least one inert gas.

In one embodiment of the present invention, the reaction in accordance with the synthesis method according to the invention is carried out at a pressure in the range from 0.1 to 5 MPa absolute, which can be the intrinsic pressure of the solvent and/or of the alcohol of the general formula (I) at the reaction temperature and/or the pressure of a gas such as nitrogen, argon or hydrogen. Preferably, the reaction in accordance with the synthesis method according to the invention is carried out at a total pressure up to 3 MPa absolute, particularly preferably at a total pressure of from 0.1 to 1 MPa absolute.

For carrying out the synthesis method according to the invention, the procedure can for example involve mixing alcohol of the general formula (I) with base and at least one oil-soluble complex compound of at least one metal of the 8th, 9th or 10th group of the Periodic Table of the Elements.

In another embodiment of the present invention, the catalyst is generated in situ. This is to be understood as meaning that oil-soluble complex compound of at least one metal of the 8th, 9th or 10th group of the Periodic Table of the Elements, preferably complex compounds of Ir(I), Ir(III), Ru(0), Ru(II) and Ru(III), particularly preferably complex compound of Ru(II) which preferably has at least one ligand $L^1$, is not isolated, but is produced in situ without further work-up by mixing a compound of a metal of the 8th, 9th or 10th group of the Periodic Table of the Elements, optionally in the presence of a reducing agent.

It is very particularly preferred to produce the catalyst by mixing Ir(I), Ir(III), Ru(0), Ru(II) or Ru(III) starting compound and Ligand $L^1$, for example by mixing Ir(I), Ir(III), Ru(0), Ru(II) or Ru(III) starting compound and ligand $L^1$ with base and alcohol of the general formula (I), optionally in the presence of a reducing agent.

Suitable iridium starting compounds are, for example, $IrCl_3$, $IrCl_3 \cdot H_2O$, $[Ir(COD)Cl]_2$, $[Ir(COE)_2Cl]_2$, $[Ir(C_2H_4)_2Cl]_2$, $[Ir(COD)OH]_2$, $[Ir(COD)MeO]_2$, $[IrCp*Cl_2]$, $[IrCpCl_2]$, $Ir_4(CO)_{12}$, $[Ir(PPh_3)_2(CO)Cl]$, $[Ir(acetylacetonate)_3]$, and $[Ir(acetylacetonate)(COD)]$.

Suitable ruthenium starting compounds are, for example, $[Ru(p\text{-cymene})Cl_2]_2$, $[Ru(benzene)Cl_2]_y$, $[Ru(CO)_2Cl_2]_y$, where y is in each case in the range from 1 to 1000, $[Ru(CO)_3Cl_2]_2$, $[Ru(COD)(allyl)]$, $RuCl_3 \cdot H_2O$, $[Ru(acetylacetonate)_3]$, $[Ru(DMSO)_4Cl_2]$, $[Ru(cyclopentadienyl)(CO)_2Cl]$, $[Ru(cyclopentadienyl)(CO)_2H]$, $[Ru(cyclopentadienyl)(CO)_2]_2$, $[Ru(Cp)(CO)_2Cl]$, $[Ru(Cp*)(CO)_2H]$, $[Ru(Cp*)(CO)_2]_2$, $[Ru(indenyl)(CO)_2Cl]$, $[Ru(indenyl)(CO)_2H]$, $[Ru(indenyl)(CO)_2]_2$, ruthenocene, $[Ru(COD)Cl_2]_2$, $[Ru(Cp*)(COD)Cl]$, $[Ru_3(CO)_{12}]$, $[Ru(PPh_3)_4(H)_2]$, $[Ru(PPh_3)_3(Cl)_2]$, $[Ru(PPh_3)_3(CO)(Cl)_2]$, $[Ru(PPh_3)_3(CO)(Cl)(H)]$, $[Ru(PPh_3)_3(CO)(H)_2]$ and $[Ru(cyclooctadienyl)(methylallyl)_2]$.

Here, Cp* means pentamethylcyclopentadienyl, COD means 1,5-cyclooctadienyl and methylallyl means 2-methylallyl.

Through the selection of the compound of a metal of the 8th, 9th or 10th group of the Periodic Table of the Elements and in particular through the selection of the Ir(I), Ir(III), Ru(0), Ru(II) or Ru(III) starting compound, it is possible to influence the selection of the further ligand(s).

In one embodiment of the present invention, ligand $L^1$ and compound of the relevant metal of the 8th, 9th or 10th group of the Periodic Table of the Elements and in particular the RID, WI), Ru(0), Ru(II) or Ru(III) starting compound can be used in stoichiometric fractions, in each case based on the central metal. In another variant, an excess of ligand $L^1$ can be used, based on metal of the 8th, 9th or 10th group of the Periodic Table of the Elements, for example 1.1 to 5 mole equivalents of $L^1$ per metal of the 8th, 9th or 10th group of the Periodic Table of the Elements.

In one embodiment of the present invention, 0.001 to 5 mol % of Ru(II) is used, based on alcohol of the general formula (I).

During the reaction in accordance with the synthesis method according to the invention, water is formed in situ as by-product. It is preferred to separate off the water which is formed, also called water of reaction for short.

In one embodiment of the present invention, the water of reaction is separated off by separating it off with an azeotropic entrainer, for example one of the aforementioned solvents, in particular one of the aforementioned aromatic solvents. In a preferred variant, the procedure involves using alcohol of the general formula (I) as azeotropic entrainer since it has a miscibility gap with water in order to separate off, or remove azeotropically, water of reaction.

Preferably, the water of reaction is removed azeotropically during the reaction with the help of a water separator.

The synthesis method according to the invention can be carried out in a wide variety of reaction vessels in which liquid reactions, optionally with a gas space, can be carried out. Suitable reaction vessels are given for example in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, chapter 3.3 "Reactors for gas-liquid reactions". Examples which may be mentioned are: stirred-tank reactors, tubular reactors and bubble-column reactors.

The synthesis method according to the invention can be carried out discontinuously, i.e. in batch mode, or continuously or semicontinuously with or without recycle. The average residence time of the reaction mass that is formed in the reaction vessel can be for example in the range from 15 minutes to 100 hours.

In one embodiment of the present invention, the method according to the invention is carried out to complete conversion of alcohol of the general formula (I). In another embodiment, the reaction is only carried out to incomplete conversion, for example to 8 to 50 mol %, preferably to 30 mol %, followed by work-up.

Without intending to give preference to a specific theory, it is thus plausible that the process according to the invention comprises essentially three reactions. Firstly, alcohol of the formula (I) is oxidatively dehydrogenated, specifically to give the aldehyde. An aldol condensation then takes place, followed by a reduction.

Implementation of the method according to the invention gives branched alcohol of the general formula (II)

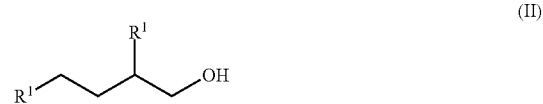

(II)

where the groups $R^1$ are different or identical and as defined above.

If a mixture of alcohol of the general formula (I) with one or more isomers is used as starting material, then a mixture of branched alcohols of the general formula (II) is usually obtained.

In one embodiment of the present invention, branched alcohol of the general formula (II.1)

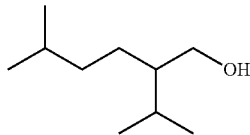
(II.1)

is obtained in a mixture with alcohol of the formula (II.1a)

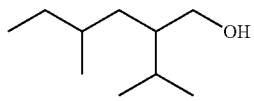
(II.1a)

In another embodiment, branched alcohol of the formula (II.2)

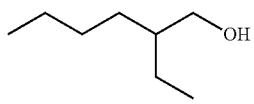
(II.2)

is obtained in a mixture with alcohol of the formula (II.2a)

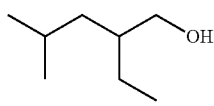
(II.2a)

In one embodiment of the present invention, a by-product obtained is acid of the formula (III), for example—if isoamyl alcohol is used as starting alcohol of the formula (I)—an acid of the formula $(CH_3)_2CH—(CH_2)—COOH.$ In one embodiment of the present invention, a by-product obtained is ester of the formula (IV), for example—if isoamyl alcohol is used as starting alcohol of the formula (I)—an ester of the formula $(CH_3)_2CH—(CH_2)—COO—(CH_2)_2—CH(CH_3)_2$ This can be saponified during the reaction.

The actual synthesis is followed by work-up. For the purpose of work-up, the procedure can involve, for example, separating off branched alcohol of the general formula (II) from unreacted alcohol of the general formula (I) and also from base and complex by distillation. Complex and base remains, with any high boilers produced, for example trimerization product of alcohol of the general formula (I), in the bottom of the distillation and can be re-used. Unreacted alcohol of the general formula (I) can likewise be returned again to the reaction. The thermal separation of branched alcohol of the general formula (II) and also of optionally formed ester can take place for example by processes known per se, preferably in an evaporator or in a distillation unit, comprising evaporator and column(s), which usually has or have a plurality of trays or packing bodies.

By means of the method according to the invention it is possible to prepare branched alcohols of the formula (I) in good yield and very good purity. For their preparation, it is possible to start not only from pure alcohol of the general formula (I), but also to use isomer mixtures, for example those which can be obtained by fermentation or other biological degradation of saccharides, in particular so-called fusel oils, for example fusel alcohol (isomer mixture of 3-methylbutanol and 2-methylbutanol).

Within the context of the present invention, the sequence of reaction and distillative work-up is also called cycle.

After 3 to 100, in particular after 3 to 10, cycles, so much by-product accumulates, for example acid of the general formula (III), that conversion and yield diminish and the ability to be mixed decreases considerably. Preferably, after 3 to 100 cycles, the method according to the invention described at the start is carried out accordingly. As a result, acid of the general formula (III) is largely removed, specifically as salt, for example to at least 80 mol %, or preferably completely removed, and the synthesis method according to the invention can be continued, for example by adding alcohol of the formula (I), optionally base, and by means of heating.

In one embodiment of the present invention, distillation is carried out before continuing with the synthesis method according to the invention to firstly at least partially remove the water remaining as a result of steps (a) and (b) and in the organic phase, for example by means of azeotropic distillation with alcohol of the general formula (I), and only then is alcohol of the general formula (I) and optionally base added in order to start the Guerbet reaction again.

The invention is illustrated further by reference to a working example.

WORKING EXAMPLE

General Procedure

The reaction was carried out under inert conditions (argon blanketing) in a 4 l three-neck flask fitted with stirrer and reflux condenser. 2.240 kg of fusel alcohol (isomer mixture of 3-methylbutanol and 2-methylbutanol, molar ratio 80:20) were introduced as initial charge, and 130 g of KOH were added thereto with stirring. The mixture was stirred for 10 minutes at room temperature and then 9.7 g of triphenylphosphane were added. The mixture was stirred for a further 10 minutes at room temperature and then 3.6 g of [Ru(COD)Cl$_2$]$_2$ were added. A pale brown suspension was formed. The pale brown suspension was transferred under nitrogen to a 4 liter jacketed glass reactor rendered inert with nitrogen and having a water separator and oblique blade stirrer and stirred for 2 hours at 100° C. A solution of 3.4 g of bis-2,6-(diethylamino)lutidine was then added, see formula,

dissolved in 60 g of fusel alcohol (isomer mixture of 3-methylbutanol and 2-methylbutanol, molar ratio 80:20). The mixture was heated to 170° C. (jacket temperature) and stirred with water separation over a period of 16 hours. The water separator was then replaced by a distillation column and unreacted fusel alcohol was distilled off (at 4 mbar$_{absolute}$ and 60° C.) and compound (II.1)

(II.1)

and crude product, comprising (II.1a)

(II.1a)

was distilled off at 3 mbar$_{absolute}$ and 110° C. The mixture was left to cool to room temperature and adjusted to atmospheric pressure by means of nitrogen. The 1st cycle was thus completed.

In the following cycles, fusel alcohol and KOH were each charged in accordance with Table 1 and the first cycle was repeated.

The results of the following cycles are summarized in Table 1.

TABLE 1

Results of cycles 1 to 4

| Cycle | Added fusel alcohol | Added KOH | Amount of water separated off | fusel alcohol distilled off | Crude product distilled off [(II.1) + (II.1a)] |
|---|---|---|---|---|---|
| 1 | 2300 g | 130 g | 150 ml | 924 g | 680 g |
| 2 | 1820 g | 140 g | 150 ml | 311 g | 1070 g |
| 3 | 1805 g | 140 g | 150 ml | 480 g | 990 g |
| 4 | 1815 g | 170 g | 170 ml | 167 g | 994 g |

After the end of the 4th cycle, there was so much solid in the distillation residue in the glass reactor that the stirrer was severely hindered and the solid was no longer completely dissolved in fusel oil. The distillation residue was mixed with 2.5 liters of water and 1 liter of fusel oil. This gave a single-phase solution which was divided into three equal portions, each of which was extracted with 0.5 liter of water. This gave in total 4 liters of aqueous phase (comprising 4 ppm of Ru compounds) and in total about one liter of organic phase (comprising 520 ppm of Ru compounds). The organic phase was introduced again into the glass reactor, and admixed with 140 g of KOH and one liter of fusel oil, and the 5th cycle was thus started. The results of cycles 5 and 6 are shown in Table 2.

TABLE 2

Results of cycles 5 and 6

| Cycle | Added fusel alcohol | Added KOH | Amount of water separated off | fusel alcohol distilled off | Crude product distilled off [(II.1) + (II.1a)] |
|---|---|---|---|---|---|
| 5 | 1000 g | 140 g | 85 ml | 523 g | 567 g |
| 6 | 2000 g | 180 g | 100 ml | 407 g | 792 g |

The invention claimed is:

1. A method for preparing a branched alcohol of formula (II)

$$R^1\text{—}CH_2\text{—}CH_2\text{—}CHR^1\text{—}CH_2\text{—}OH \quad (II)$$

comprising subjecting at least one alcohol of formula (I) to a Guerbet reaction $$R^1\text{—}CH_2\text{—}CH_2\text{—}OH \quad (I);$$

in the presence of an oil-soluble complex compound of a metal from the 8th, 9th or 10th group of the Periodic Table of the Elements, wherein the complex compound comprises a ligand $L^1$ which is at least bidentate, and a coordination site of $L^1$ is a nitrogen atom, following said reaction, working up a mixture comprising at least one of said alcohol of formula (I) and said branched alcohol of formula (II), and said oil-soluble complex compound; and an acid of formula (III)

$$R^1\text{—}CH_2\text{—}COOH \quad (III),$$

in a form of one of its salts, wherein $R^1$ is a $C_2$-$C_{10}$-alkyl, linear or branched, wherein the working up is carried out by treating the mixture with water which can comprise an alkali metal hydroxide, and extracting the salt or salts of acid of formula (III), thereby forming a worked-up mixture, and subjecting the worked-up mixture to a further Guerbet reaction for preparing the branched alcohol of formula (II) after addition of further alcohol of formula (I), and optionally, a base.

2. The method according to claim 1, wherein the mixture comprises both an alcohol of formula (I) and a branched alcohol of formula (II).

3. The method according to claim 1, wherein the method is carried out at a temperature of from 5 to 60° C.

4. The method according to claim 1, wherein $R^1$ is each independently selected from the group consisting of ethyl, n-propyl, n-butyl and isopropyl.

5. The method according to claim 1, wherein the oil-soluble complex compound is a complex compound of at least one selected from the group consisting of Ir(I), Ir(III), Ru(0), Ru(II) and Ru(III).

6. The method according to claim 1, wherein $L^1$ is at least one selected from the group consisting of a bidentate ligand and a tridentate ligand, which coordinates with the a central metal via nitrogen atom and optionally a carbene carbon atom.

7. The method according to claim 1, wherein the oil-soluble complex compound comprises a further ligand selected from the group consisting of CO, a pseudohalide, an organic carbonyl compound, an aromatic, an olefin, a phosphane, a hydride, and a halide.

8. The method according to claim 1, wherein $L^1$ is a compound of formula (V)

(V)

wherein
$R^3$ is selected from the group consisting of hydrogen and $C_1$-$C_5$-alkyl, n is zero or one,
X$^1$ is selected from the group consisting of hydrogen, C$_1$-C$_5$-alkyl and (CH$_2$)$_{n+1}$—X$^2$,
X$^2$ is selected from the group consisting of NR$^4$R$^5$, 2-pyridyl and imidazol-2-ylidenyl of formula

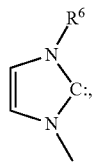

R$^4$ and R$^5$ are identical or different and selected from the group consisting of C$_1$-C$_{10}$-alkyl, C$_3$-C$_{10}$-cycloalkyl, benzyl, and phenyl, unsubstituted or mono- or polysubstituted with C$_1$-C$_3$-alkyl,
R$^6$ is selected from the group consisting of C$_1$-C$_{10}$-alkyl, C$_3$-C$_{10}$-cycloalkyl, benzyl, and phenyl, unsubstituted or mono- or polysubstituted with C$_1$-C$_3$-alkyl.

9. The method according to claim 1, wherein L$^1$ is a compound of formula (VI)

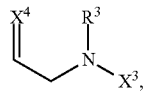

(VI)

wherein
R$^3$ is selected from the group consisting of hydrogen, C$_1$-C$_{10}$-alkyl, C$_3$-C$_{10}$-cycloalkyl, benzyl and phenyl,
X$^3$ is selected from the group consisting of hydrogen, C$_1$-C$_5$-alkyl and CH=X$^4$,
X$^4$ is NR$^4$, and
R$^4$ is selected from the group consisting of C$_1$-C$_{10}$-alkyl, C$_3$-C$_{10}$-cycloalkyl, benzyl, and phenyl, unsubstituted or mono- or polysubstituted with C$_1$-C$_3$-alkyl.

10. The method according to claim 1, wherein L$^1$ is a compound of formula (VII)

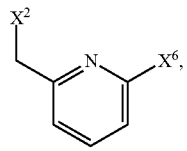

(VII)

wherein
X$^6$ is selected from the group consisting of hydrogen, C$_1$-C$_5$-alkyl and CH$_2$—X$^2$,
X$^2$ is selected from the group consisting of NR$^4$R$^5$, 2-pyridyl, and imidazol-2-ylidenyl of formula

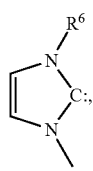

R$^4$ and R$^5$ are different or identical and selected from the group consisting of C$_1$-C$_{10}$-alkyl, C$_3$-C$_{10}$-cycloalkyl, benzyl, and phenyl, unsubstituted, or mono- or polysubstituted with C$_1$-C$_3$-alkyl, and
R$^6$ is selected from the group consisting of C$_1$-C$_{10}$-alkyl, C$_3$-C$_{10}$-cycloalkyl, benzyl, and phenyl, unsubstituted or mono- or polysubstituted with C$_1$-C$_3$-alkyl.

11. The method according to claim 1, wherein L$^1$ is a compound of formula (VIII)

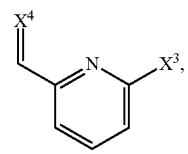

(VIII)

wherein
X$^3$ is selected from the group consisting of hydrogen, C$_1$-C$_5$-alkyl and CH=X$^4$,
X$^4$ is different or identical and is N—R$^4$, and
R$^4$ is selected from the group consisting of C$_1$-C$_{10}$-alkyl, C$_3$-C$_8$-cycloalkyl, benzyl and phenyl, unsubstituted or mono- or polysubstituted with C$_1$-C$_3$-alkyl.

12. The method according to claim 1, wherein L$^1$ is a compound of formula (IX)

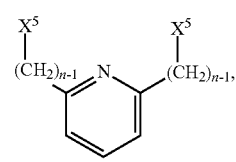

(IX)

wherein
n is identical or different and in each case zero or one
X$^5$ is in each case identical and selected from the group consisting of NR$^4$R$^5$, 2-pyridyl and imidazol-2-ylidenyl of formula:

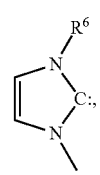

R$^4$ and R$^5$ are different or identical and selected from the group consisting of C$_1$-C$_{10}$-alkyl, C$_3$-C$_{10}$-cycloalkyl, benzyl, and phenyl, unsubstituted or mono- or polysubstituted with C$_1$-C$_3$-alkyl, and
R$^6$ is selected from the group consisting of C$_1$-C$_{10}$-alkyl, C$_3$-C$_{10}$-cycloalkyl, benzyl, and phenyl, unsubstituted or mono- or polysubstituted with C$_1$-C$_3$-alkyl.

13. The method according to claim 1, wherein in the treating, the water and the mixture have a volume ratio of from 0.5:1 to 2:1.

14. A method for preparing a branched alcohol of formula (II),

R$^1$—CH$_2$—CH$_2$—CHR$^1$—CH$_2$—OH        (II), the method comprising reacting an alcohol of formula (I)

$R^1$—$CH_2$—$CH_2$—OH     (I), wherein $R^1$ is a $C_2$-$C_{10}$-alkyl, linear or branched,
in the presence of an oil-soluble complex compound of a metal from the 8th, 9th or 10th group of the Periodic Table of the Elements, wherein the complex compound comprises a ligand $L^1$ which is at least bidentate, and a coordination site of $L^1$ is a nitrogen atom wherein by-products selected from acids of formula (III)

$R^1$—$CH_2$—COOH     (III), are separated off in a form of one of their salts by a method according to claim 1.

15. The method according to claim 1, wherein the alcohol of formula (I) is in the form of an isomeric mixture thereof, wherein each alcohol has formula (I).

16. The method according to claim 14, wherein the alcohol of formula (I) is in the form of an isomeric mixture thereof, wherein each alcohol has formula (I).

17. The method according to claim 1, wherein the alcohol of formula (I) is in the form of an isomeric mixture, wherein at least one alcohol does not have formula (I).

18. The method according to claim 14, wherein the alcohol of formula (I) is in the form of an isomeric mixture, wherein at least one alcohol does not have formula (I).

19. The method according to claim 17, wherein the isomeric mixture is of 3-methylbutanol and 2-methylbutanol.

20. The method according to claim 18, wherein the isomeric mixture is of 3-methylbutanol and 2-methylbutanol.

* * * * *